United States Patent
O'Brien et al.

(10) Patent No.: US 9,678,016 B2
(45) Date of Patent: Jun. 13, 2017

(54) FLOW ANALYZER FOR HARSH ENVIRONMENTS

(71) Applicant: J.M. Canty Inc, Buffalo, NY (US)

(72) Inventors: Paul J. O'Brien, East Aurora, NY (US); Thomas M. Canty, Amherst, NY (US); David E. Jean, West Seneca, NY (US); Justin R. Hallbach, Clarence, NY (US); Michael F. Rizzo, Blasdell, NY (US)

(73) Assignee: J.M. CANTY INC, Buffalo, NY (US)

( * ) Notice: Subject to any disclaimer, the term of this patent is extended or adjusted under 35 U.S.C. 154(b) by 0 days.

(21) Appl. No.: 14/603,400

(22) Filed: Jan. 23, 2015

(65) Prior Publication Data

US 2016/0216213 A1 Jul. 28, 2016

(51) Int. Cl.
*G01N 1/10* (2006.01)
*G01N 21/85* (2006.01)
*G01N 21/05* (2006.01)
*G01N 15/14* (2006.01)
*G01N 15/02* (2006.01)
*G01N 21/09* (2006.01)
(Continued)

(52) U.S. Cl.
CPC .......... *G01N 21/85* (2013.01); *G01N 15/0227* (2013.01); *G01N 15/1434* (2013.01); *G01N 21/05* (2013.01); *G01N 21/09* (2013.01); *G01N 21/15* (2013.01); *G01N 2021/0389* (2013.01); *G01N 2021/052* (2013.01); *G01N 2021/151* (2013.01); *G01N 2021/8557* (2013.01); *G01N 2201/02* (2013.01); *G01N 2201/062* (2013.01); *G01N 2201/12* (2013.01)

(58) Field of Classification Search
CPC .... G01N 1/10; G01N 1/20; F17D 3/00; F17D 5/00; B08B 3/00; A61B 5/00; B65G 53/34
See application file for complete search history.

(56) References Cited

U.S. PATENT DOCUMENTS 4,878,785 A * 11/1989 Heron ........................ B24C 5/04
239/590
5,699,794 A * 12/1997 Fleck .................... G01N 35/021
128/920

(Continued)

FOREIGN PATENT DOCUMENTS

DE 2217026 A1 10/1973
EP 2980557 A1 2/2016
(Continued)

*Primary Examiner* — Tarifur Chowdhury
*Assistant Examiner* — Jamil Ahmed
(74) *Attorney, Agent, or Firm* — Leydig, Voit & Mayer, Ltd.

(57) ABSTRACT

A flow analyzer includes a flow body having a single-piece construction. The flow body includes a flow path extending through the flow body along a flow direction between opposing inlet and outlet ports and an enclosed wiring conduit extending substantially transverse to the flow direction between a first side of the flow body and a second side of the flow body. The enclosed wiring conduit is isolated from the flow path. An illumination unit is disposed on the first side of the flow body and configured to illuminate fluid within the flow path. An observation unit is disposed on the second side of the flow body and configured to visually observe the fluid within the flow path.

9 Claims, 6 Drawing Sheets

(51) Int. Cl.
　　　*G01N 21/15* (2006.01)
　　　*G01N 21/03* (2006.01)

(56) References Cited

U.S. PATENT DOCUMENTS

| | | |
|---|---|---|
| 6,359,742 B1 | 3/2002 | Canty et al. |
| 6,771,366 B2 | 8/2004 | Canty et al. |
| 6,782,184 B2 | 8/2004 | Canty et al. |
| 7,369,226 B1 | 5/2008 | Hewitt |
| 8,297,302 B2 | 10/2012 | O'Brien et al. |
| 9,091,618 B1 * | 7/2015 | Baratto ................ G01N 1/2035 |
| 2004/0066509 A1 * | 4/2004 | Canty .................... G01N 21/05 356/246 |
| 2011/0240134 A1 * | 10/2011 | O'Brien .............. F16K 37/0058 137/15.01 |
| 2016/0069856 A1 | 3/2016 | Gorritxategi et al. |

FOREIGN PATENT DOCUMENTS

| | | |
|---|---|---|
| WO | WO 2004097381 A1 | 11/2004 |
| WO | WO 2007143474 A1 | 12/2007 |
| WO | WO 2011107102 A1 | 9/2011 |
| WO | WO 2014154915 A1 | 10/2014 |

* cited by examiner

FLOW ANALYZER FOR HARSH ENVIRONMENTS

FIELD

The application relates to devices for observing and analyzing the contents of a process pipeline or vessel, and more particularly for an analysis device with features that are suitable for harsh environments.

BACKGROUND

In certain industries, it is desirable to observe and analyze the contents within an enclosed pipeline or vessel without substantially disrupting the flow or process therein. For example, U.S. Pat. No. 6,771,366, which is incorporated by reference herein in its entirety, describes a flow cell device system that includes an optical flow cell that enables automatic visual analysis and inspection of fluids for various characteristics including particle size, shape, color, and count, among others. The system includes two viewing ports, each containing a transparent glass window to allow illumination and/or viewing of a fluid in an aperture defined between the two viewing ports.

Advances in such flow cells have been made over time. For example, U.S. Pat. Nos. 6,782,184 and 8,297,302, which are incorporated by reference herein in their entirety, describe spray ring devices that provide for cleaning of an internal process window. These spray rings are configured to discharge a fluid onto the window surface in order to dislodge any particles or substances on the window that are hindering observation of the flow through the flow cell.

While the above-described structures are excellent for their intended functions, none of these devices are specifically designed to operate in extremely harsh environments. Thus, while these devices are adequate for many environments, they lack features that would allow them to operate in the harshest of environments.

SUMMARY

In an embodiment, the present invention provides a flow analyzer includes a flow body having a single-piece construction. The flow body includes a flow path extending through the flow body along a flow direction between opposing inlet and outlet ports and an enclosed wiring conduit extending substantially transverse to the flow direction between a first side of the flow body and a second side of the flow body. The enclosed wiring conduit is isolated from the flow path. An illumination unit is disposed on the first side of the flow body and configured to illuminate fluid within the flow path. An observation unit is disposed on the second side of the flow body and configured to visually observe the fluid within the flow path.

BRIEF DESCRIPTION OF THE DRAWINGS

The present invention will be described in even greater detail below based on the exemplary figures. The invention is not limited to the exemplary embodiments. All features described and/or illustrated herein can be used alone or combined in different combinations in embodiments of the invention. The features and advantages of various embodiments of the present invention will become apparent by reading the following detailed description with reference to the attached drawings which illustrate the following.

DETAILED DESCRIPTION

Figure 1:
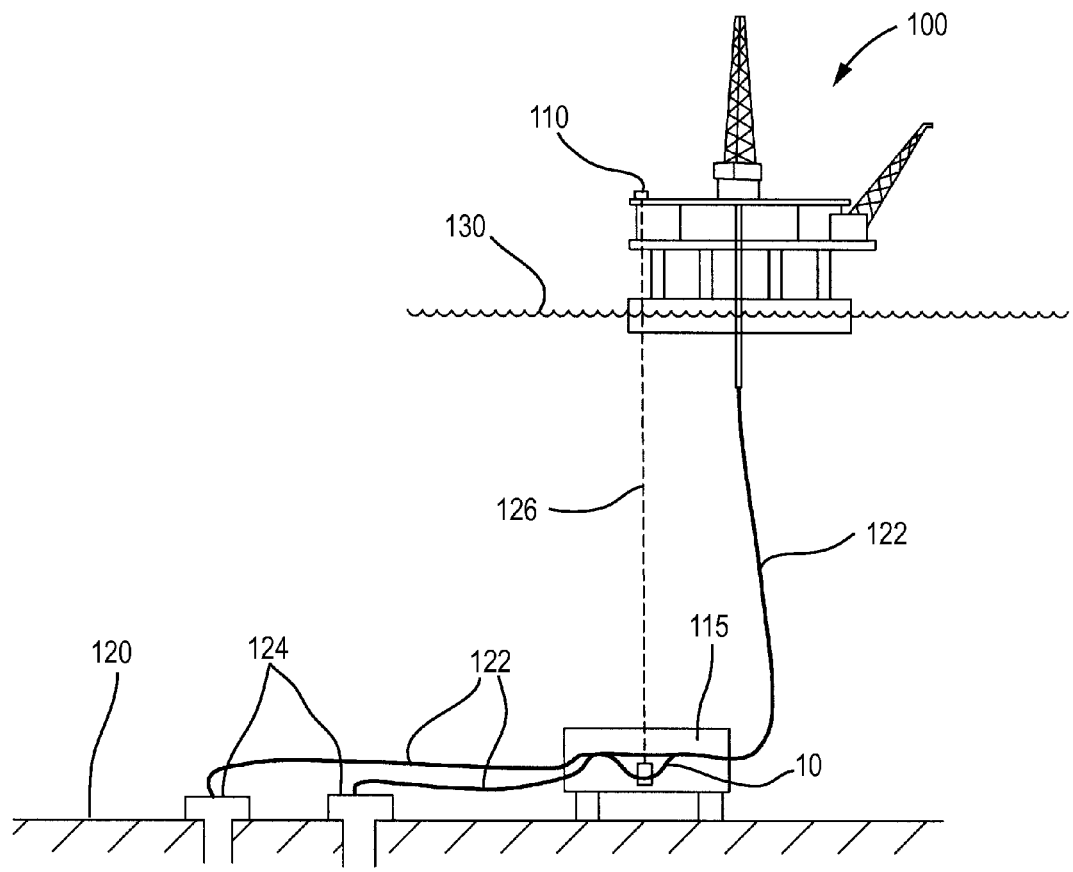
FIG. 1 shows a schematic illustration of the use of a flow analyzer in a harsh environment.

FIG. 1 depicts a flow analyzer 10 disposed within harsh environmental conditions that analyzes the contents of a fluid flow and sends the corresponding analytical data to a communications device 110 at a base station 100. In the embodiment of FIG. 1, the flow analyzer 10 is disposed at a remote distance from the base station 100. In the context of this disclosure, the term "remote" is used to indicate a distance of at least one hundred feet, and including distances of several hundred feet to one or more miles. Of course, the flow analyzer 10 could also be disposed nearer to the base station 100, which itself may also be located at the sea floor.

In the illustrated embodiment shown in FIG. 1, the flow analyzer 10 is configured as a subsea analyzer and is located in a harsh underwater environment. To accommodate these conditions, the analyzer 10 is adapted to operate at the extreme pressure and corrosive conditions existing near the sea floor 120. The flow analyzer 10 in FIG. 1 is specifically configured to analyze the fluid flow in flow lines 122 extending from at least one subsea well 124. Although FIG. 1 shows two subsea wells 124, any number of subsea wells is contemplated herein, with flow lines running to each well. The analyzer 10 is positioned near the opening of the well 124 and analyzes a portion of the flow passing through the flow line 122. In some embodiments, such as the embodiment illustrated in FIG. 1, the analyzer 10 can be disposed within a subsea manifold structure 115, which can rest on the sea floor 120. The subsea manifold 115 can act as a separation module for the flow lines 122 connected to the well heads 124, and can also house the analyzer 10. It is also contemplated, however, that in some embodiments, the analyzer 10 can be connected directly to the flow lines 122 without being housed in a subsea manifold.

In this embodiment, the base station 100 is a facility intended to extract and process oil and/or natural gas from the wells 124. For example, the base station 100 is specifically depicted as a semi-submersible drilling rig, but could also be a similar facility located on a ship. The station could also be located on the sea floor. In the subsea environment depicted, the base station 100 is disposed in fluid communication with the flow line 122. Specifically, the fluid in the flow line 122 is flowing to the base station 100. Likewise, the analytical data from the flow analyzer 10 is sent to the base station 100, where it is received by the communications device 110. Similarly, in many other embodiments, the base station 100 will be disposed in communication with the flow line 122 of interest, either at the source of the flow or at the destination of the flow. Alternatively, the base station 100 may be physically separated from the flow line 122 and merely receive data from the flow analyzer 10. For example, in the context of the subsea analyzer 10 shown in FIG. 1, the base station 100 could be disposed on the shore or on a central control ship that oversees the operations of various extraction and processing facilities. In a preferred embodiment of the subsea configuration, the base station 100 is at or above the water surface 130, such as the semi-submersible oil platform shown in FIG. 1.

The flow analyzer 10 includes a control system 50 that will be described in more detail below. In the embodiment shown in FIG. 1, the control system of the flow analyzer includes a data output for establishing a communications link 126 with a data input of the communications device 110 on the base station 100. Using the communications link 126, the flow analyzer 10 is able to send analytical data representative of the flow to the communications device 110 on the base station 100. The communications link 126 can be established with a physical connection between the flow analyzer 10 and communications device 110, for example using a wired connection or fiber optic connection, or it may be established with a wireless connection.

Figure 2A:
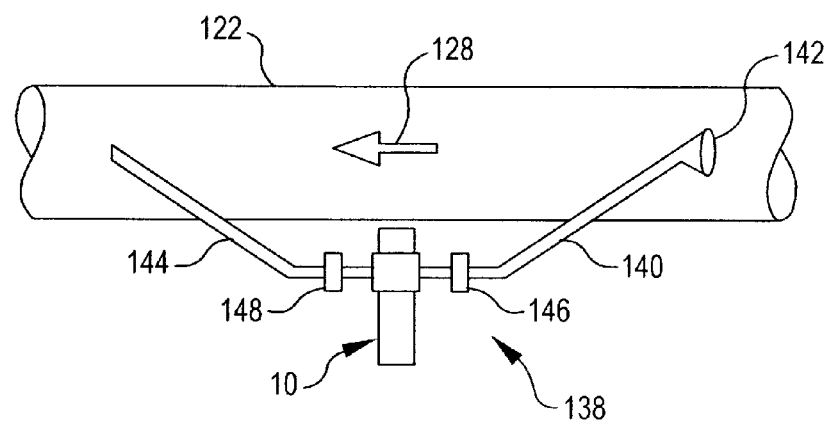
FIG. 2A shows an interface of a flow analyzer with a flow line in accordance with an embodiment of the invention.

FIG. 2A shows an embodiment of a fluid interface 138 between the flow analyzer 10 and the flow line 122. In this embodiment, the flow analyzer 10 captures a portion of the flow 128 using an intake 140 that has direct access to the fluid within the flow line 122. For example, in the embodiment illustrated in FIG. 2A, the flow line 122 is a large channel or conduit through which the fluid flows, and the intake 140 is in the form of a smaller pipe that extends into the interior of flow line 122. The intake 140 includes an intake opening 142 in a vicinity of the center of the flow line 122 so as to promote the likelihood that the intake 140 is able to feed the flow analyzer 10 with a sample of the flow that is most representative of the majority of fluid passing through the flow line 122. However, it is also possible that the intake opening 142 be a simple access port disposed in a wall of the flow line 122, or some other arrangement that is able to access a sample of the fluid in the flow line. After passing through the flow analyzer 10, the sample may rejoin the fluid in the flow line 122 by way of a return 144. While in many embodiments, such as the subsea configuration shown in FIG. 1, there is both an economic and environmental advantage to returning the sample to the flow line 122, it is not necessary to the operation of the flow analyzer 10 that the sample be returned to the flow line 122. As an alternative, the sample withdrawn from the flow line 122 could be stored or discharged in another manner.

In the embodiment illustrated in FIG. 2A, control of the fluid flowing through the flow analyzer 10 is enabled using two valves 146 and 148, respectively disposed upstream and downstream of the flow analyzer 10. Any appropriate valve for hindering the flow may be used, but shut-off valves that can completely stop the flow of fluid through the flow analyzer 10 are preferable. While the fluid flow through the flow analyzer 10 can, of course, be stopped using a single shut-off valve, the use of valves 146, 148 on either side of the flow analyzer 10 enable the analyzer to be removed entirely from the system, for example for maintenance or replacement, without the threat of fluid from the flow line 122 escaping from the system. In this regard, it is also possible for the downstream valve 148 to be a check valve.

The use of two valves 146, 148 in the fluid interface 138 allows maintenance to be performed on the flow analyzer 10 without disrupting the flow in the main flow line 122. In a method for removing the flow analyzer 10, the valves 146, 148 are both closed without stopping fluid flow within the main flow line 122. The closing of both valves can be actively carried out, such as physically shutting the valves, or at least the return valve 148 can be closed passively, for example if valve 148 is a check valve. Once the valves are closed, the flow analyzer 10 may be removed from the fluid interface 138 and either repaired or replaced. After the flow analyzer 10 is reinserted into the fluid interface 138, the valves 146, 148 may be reopened so that the flow analyzer can operate once again.

Advantageously, as shown in FIG. 2A, the intake 140 can taper inward from the opening 142, for example in the shape of a funnel. As a result of the constriction associated with the decrease in diameter of the intake 140 in the direction of the flow, the fluid is caused to accelerate as it flows through the analyzer 10. With the increase in velocity, the flow is able to keep larger particles suspended, which is an advantage in many analysis systems, where observation of solids within the flow may be a primary objective of the analysis. In embodiments such as that shown in FIG. 2A having a funnel-shaped opening 142, the relatively large area of the intake opening can cause interruption of the fluid flow 128 within the flow line 122, which can result in a decrease in flow velocity downstream of the opening as compared to at the opening or upstream of the opening. The reduced velocity can result in a pressure differential within the flow line 122 between the opening and the return 144, which can drive flow through the analyzer as the fluid drawn into the analyzer flows from a relatively high to low pressure.

Figure 2B:
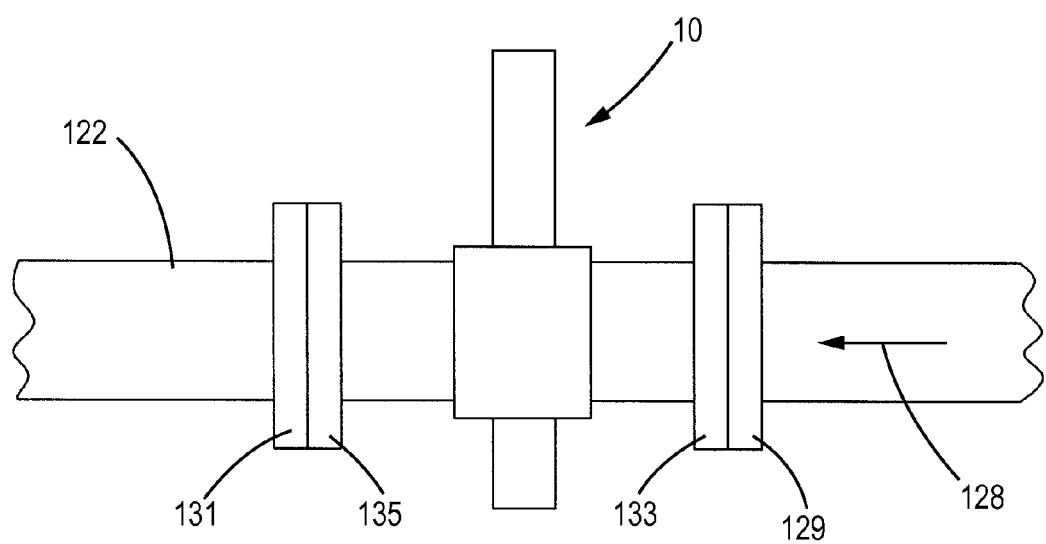
FIG. 2B shows an interface of a flow analyzer with a flow line in accordance with an another embodiment of the invention.

FIG. 2B illustrates another embodiment in which the flow analyzer 10 is disposed directly in-line with the flow line 122. In such embodiments, the analyzer 10 can engage directly with the fluid flow 128 without using an intake or return, such as shown in FIG. 2A. The in-line configuration of the analyzer 10 shown in FIG. 2B can be disposed between first and second flow line flanges 129, 131. The first flow line flange 129 can connect to a first analyzer flange 133, and the second flow line flange 131 can connect to a second analyzer flange 135 using bolts, welding, or any other suitable connecting method. In some embodiments, the analyzer 10 can be installed or removed from between the flow line flanges 129, 131 as a single part, thus simplifying the installation or removal process. During such installation or removal, valves disposed at or near the flow line flanges 129, 131 can be closed in order to halt the flow 128 in the flow line 122 at the flow line flanges 129, 131, and opened to flow through the analyzer 10 once installed. In other embodiments, such as the embodiment shown in FIG. 8, fluid flow diverted to the analyzer from the fluid line 122 can be sampled using a single-point entry.

Figure 3:
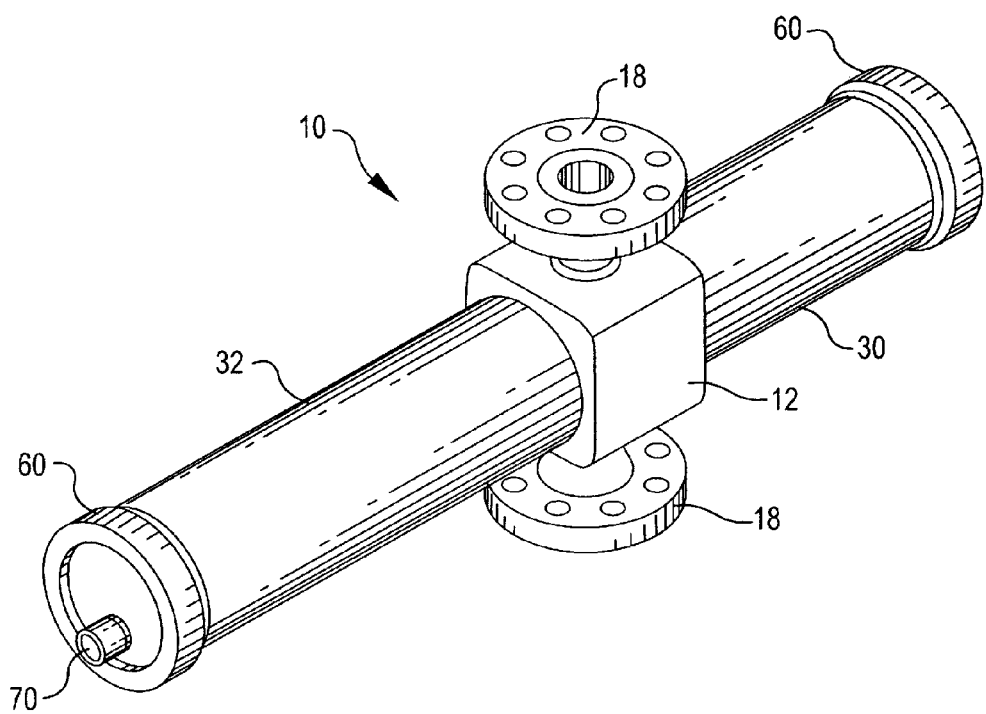
FIG. 3 shows a perspective view of a flow analyzer in accordance with an embodiment of the invention.
Figure 4:
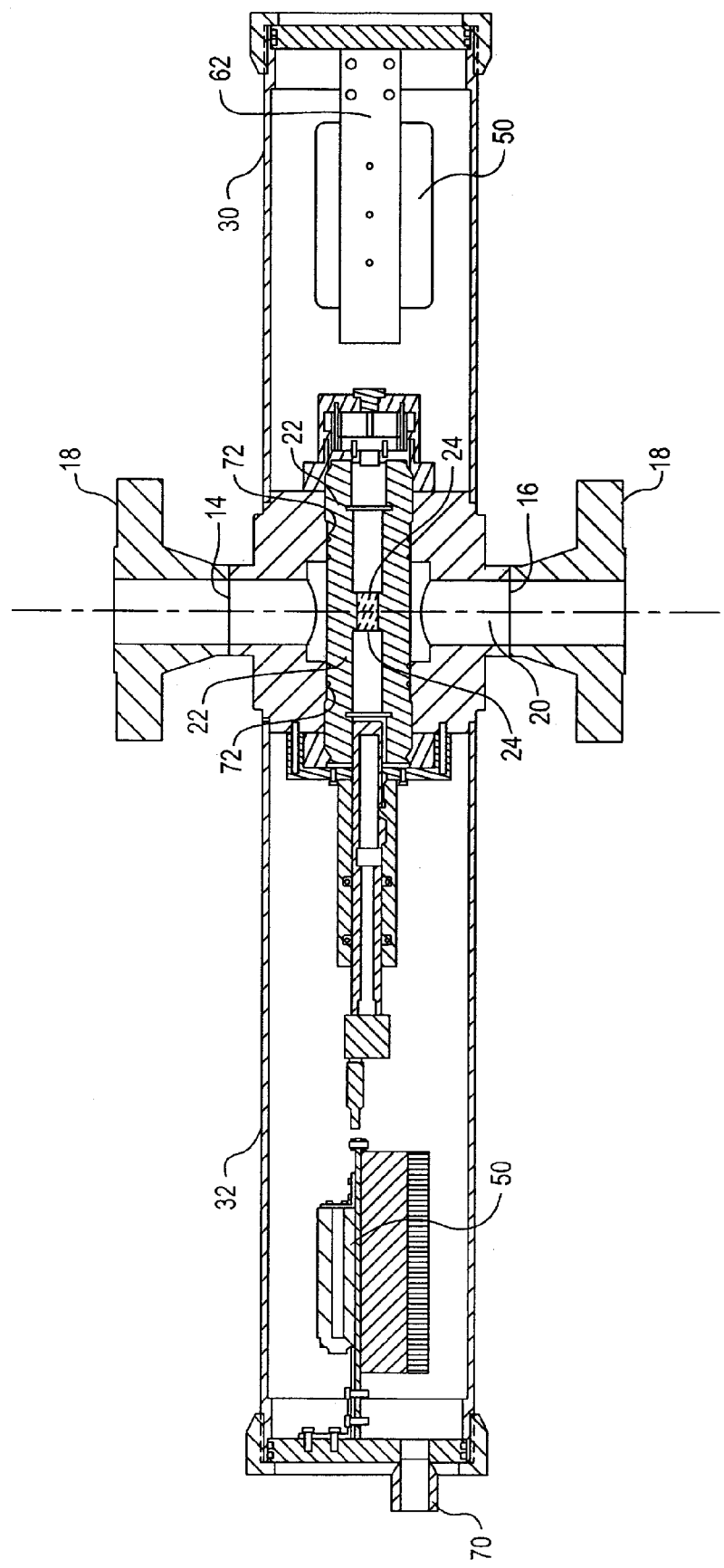
FIG. 4 shows a cross-sectional view of the flow analyzer of FIG. 3.
Figure 5:
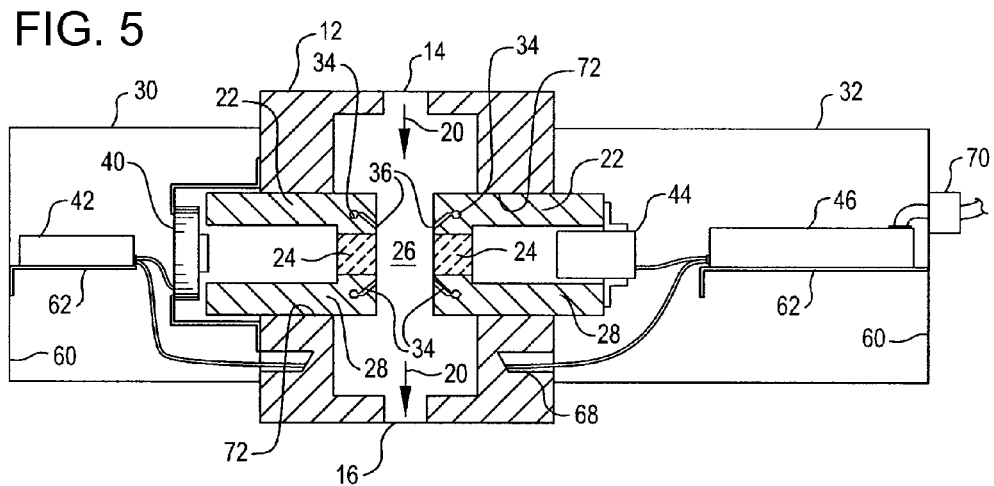
FIG. 5 shows a schematic representation of a cross-section of a flow analyzer in accordance with an embodiment of the invention, the cross-section being aligned with a flow path through the analyzer.

FIGS. 3 and 4 illustrate an embodiment of the flow analyzer 10 shown in more detail. As shown, the flow analyzer 10 includes a flow body 12 including an inlet port 14 and an outlet port 16 (see FIG. 4), which are respectively coupled to intake 140 and return 144 of the fluid interface 138 with the flow line 122. The flow body 12 can advantageously be formed as a single monolithic structure, for example being either machined from one piece of material or cast in a single piece. Alternatively, the flow body 12 could be a single piece that is formed from individual pieces that are joined by a chemical connection forming a single unitary structure, such as a single weldment. Further still, the flow body 12 could be several pieces that are joined by a material connection, such as brazing, or a mechanical connection, such as bolts. The flow body 12 can be directly connected to the intake 140 and return 144 of the fluid interface 138, or can attached to intermediate connection elements 18, such as the flange connections shown in FIG. 3.

Between the inlet port 14 and outlet port 16 of the flow body 12 is a path 20 for the extracted fluid that passes through an aperture 26 between two viewing members 22. Each of the viewing members 22 include a corresponding window 24 allowing illumination or observation of the fluid within the aperture 26. In a preferred embodiment, the windows are constructed of glass that is fused directly to an annular metal frame 28 of the viewing member 22, for example as described in U.S. Pat. No. 6,359,742, which is hereby incorporated by reference herein in its entirety. Preferably, the construction of the viewing members 22 and flow body 12 is sturdy enough to handle fluids having high pressures, such as pressures of up to and exceeding 6000 pounds per square inch (psi). The sturdy fused glass-to-metal construction enables a wide field of view for a broader view of the flow stream through the aperture 26 and thus, better analytical accuracy. Moreover, this construction allows a larger flow body to process more fluid in less time.

In cooperation with the flow body 12 and corresponding viewing members 22, the flow analyzer 10 includes an illumination system disposed in an illumination housing section 30 positioned on one side of the flow body 12 and an observation system disposed in an observation housing section 32 positioned on an opposing side of the flow body. In this instance, the overall housing of the flow analyzer includes the flow body 12 as well as the illumination and observation housing sections 30, 32. In the illustrated embodiment, the illumination system includes an illumination device 40 and an illumination controller 42. In this embodiment, the controller 42 is a distinct unit disposed within the illumination housing section 30. However, it is also possible for the control of the illumination device 40 to be carried out by a primary control unit of the flow analyzer, where the illumination controller 42 is a sub-component or module of the primary control unit. The illumination device 40 may include any controllable light source that can be operated to illuminate the fluid within aperture 26. For example, the illumination device 40 may be an electrically powered light source. Preferably, the light source can be activated and deactivated at high speeds. Examples of such devices include electroluminescent devices, such as light emitting diodes, or lasers. Alternatively, the illumination device 40 could be another light source, such as a lamp. The illumination controller 42 is operable to activate and deactivate the illumination device 40 so as to illuminate the fluid in a desired manner, and may include components for operating the light source in a specialized manner, such as a strobe generator.

The observation system includes an imaging device 44, such as a camera, an imaging controller and a computational unit. The camera can be any appropriate device for capturing images of the fluid within the flow body 12, including a still digital camera or a video camera. Other methods of obtaining image data of the flow are also possible, for example, using magnetic imaging, sonar, radar, or any other means to determine spatial characteristics of the flow within aperture 26. Any device capable of obtaining such image data should also be considered an imaging device within the meaning of the present description. In the illustrated embodiment, the imaging controller and computational unit are both integrated into a single control unit 46 that both operates the imaging device 44 and that performs computations to analyze the recorded images in order to generate analytical data about the fluid flow within the flow analyzer 10.

The illumination controller, imaging controller, and computational unit are all part of a control system 50 disposed within the flow analyzer 10 that operates the analyzer and computes analytical data associated with the flow of fluid passing therethrough. In the illustrated embodiment, the control system 50 is formed by the illumination controller 42 in the illumination housing section 30 and the control unit 46, that forms both the imaging controller and computational unit, in the observation housing section 32. However, it is also possible for the control system 50 to be consolidated into a single unit, or to be spread over additional modules that perform discrete tasks. The control system 50, preferably includes at least one electronic controller that operates in a logical fashion to perform operations, execute control algorithms, store and retrieve data and other desired operations. These controllers may include or access memory, secondary storage devices, processors, and any other components for running an application. The memory and secondary storage devices may be in the form of read-only memory (ROM) or random access memory (RAM) or integrated circuitry that is accessible by the controller. Various other circuits may be associated with the control system such as power supply circuitry, signal conditioning circuitry, driver circuitry, and other types of circuitry. The term "controller" is meant to be used in its broadest sense to include one or more controllers and/or microprocessors that may be associated with the control system and that may cooperate in controlling various functions and operations of the components of the flow analyzer. The functionality of the control system 50 may be implemented in hardware and/or software without regard to the functionality.

In operation, the computational unit receives image data from the imaging device 44 and uses algorithms to analyze the images for determining certain characteristics of the flow, such as turbidity, particle size, shape, count and color, particle velocity and fluid color, haze and opacity. As a result of analyzing the images, the computational unit produces analytical data that includes at least one measure of a determined flow characteristic and excludes any image data. The computed analytical data is then sent without any image data through a data output of the control system 50 along the communications link 126 to the base station 100. Once the analytical data has been determined by the computational unit, the image data can be deleted or stored locally. It should be appreciated that, if the image data is stored, it could be sent to the base station 100 via the communications link 126 at an appropriate time, for example when the flow is not being analyzed. In this regard, however, it should be understood that the image data, in such an embodiment, is not sent to the base station 100 with the analytical data. In other words, a series of analytical data is computed from the image data and sent to the base station 100 before the image data itself is sent to the base station 100. For example, the analytical data could be computed from a series of distinct images and repeatedly sent to the base station before the image data is sent. For instance, twenty, one hundred or one thousand images could be analyzed and the corresponding analytical data sent to the base station before any of the corresponding image data is sent to the base station. Similarly, in the case of the image data being more continuous, such as video imaging, the analytical data could be computed and sent to the base station after a certain time frame, such as after at least 10 minutes, at least one hour, or at least one day, before any image data is sent to the base station 100.

In some embodiments, images and/or video can be sent from the flow analyzer to the base station controller 110, where the images/video could be analyzed should the subsea analyzer component not function properly.

To the extent that sending the analytical data from the flow analyzer 10 to the base station 100 is a characteristic feature of a particular embodiment of the invention, it should be understood that the analytical data is sent from a data output of the control system 50 disposed within the housing of the flow analyzer. In such an instance, the housing may be considered the structure in the vicinity of the flow body, for example, within 10 feet of the flow body. Of course, it is also possible that the housing be larger. There are other characteristics that may define the data output of the control system 50 as being within the housing. For example, in the illustrated embodiments of FIGS. 3-6, the housing is formed of two housing sections 30, 32. Each of these housing sections 30, 32 includes an open end that is attached to one side of the flow body, thereby forming a cavity that is in fluid communication with an outer surface of the flow body. If the data output of the control system 50 were disposed within such a cavity, this too could be considered to be within the housing of the flow analyzer 10. Of course, the data output could be disposed in a section of the housing that is sealed off from the outer surface of the flow body 12 and still be considered within the flow analyzer housing.

Figure 6:
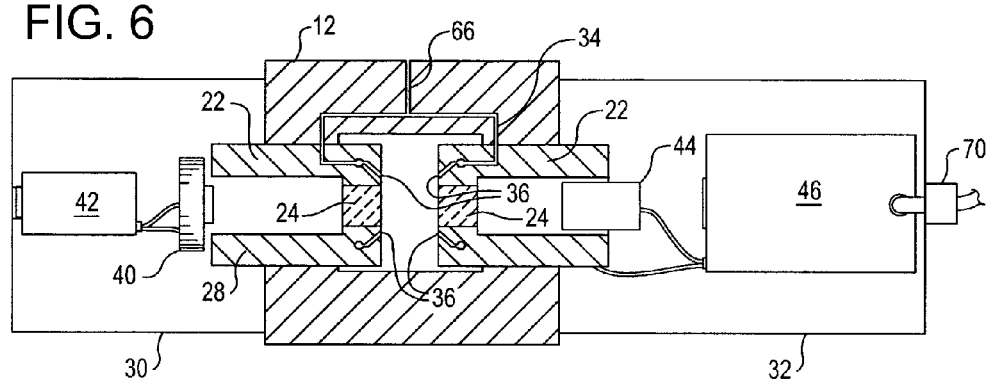
FIG. 6 shows a schematic representation of a cross-section that is transverse to the cross-section of FIG. 5.
Figure 7:
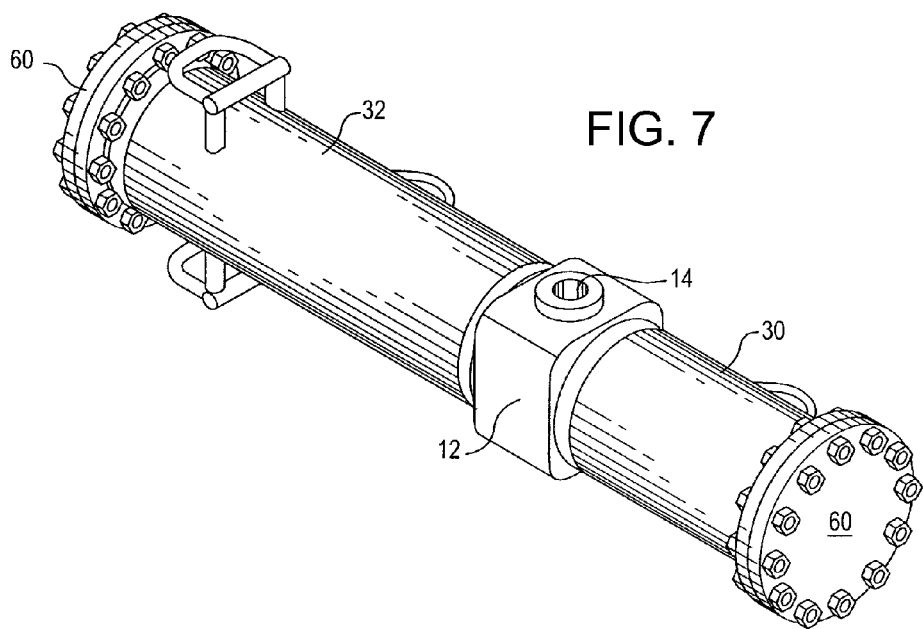
FIG. 7 shows a perspective view of another flow analyzer in accordance with an embodiment of the invention.

As stated above, the housing of the flow analyzer 10 can be formed by two housing sections 30, 32 and the flow body 12, as shown in FIGS. 3-6. In particular, the housing sections 30, 32 can be attached to opposing sides of the flow body, preferably with a sealed connection, such as a welded connection. Other types of connections are also possible, such as a mechanical connection with the appropriate seals to prevent leakage into the housing, if necessary. In a subsea environment, as described above, it can be advantageous for the housing sections 30, 32 to be round or cylindrical. The cylindrical shape is best suited to resist external or internal pressure with a minimum of material weight per volume enclosed. This can be especially important with regard to cost and weight where there is a large pressure environment surrounding the flow analyzer 10. To provide a secure enclosure, the ends of the respective housing sections 30, 32 can be closed off using a cap 60. The cap 60 can be embodied as a single disk with bolt holes for bolting to a flanged end connector of the respective housing section 30, 32, such as is shown in FIG. 7. Alternatively, the cap 60 can be embodied as multiple pieces, such as a flat disk that is held on the end of the respective housing section 30, 32 using a threaded retainer, as shown in FIGS. 3 and 4. Other cap configurations are also possible. In the case of a cylindrical housing, it may be advantageous for the operational elements of the flow analyzer 10 to be secured within the housing using brackets 62 that are connected to the end caps 60 or flow body 12. Such a configuration avoids the necessity for making any connections with the cylindrical wall of the housings 30, 32, allowing these wall sections to be thinner and lighter. Of course, it is possible to connect the operational elements to the cylindrical wall, for example, using an annular bracket that braces against, or directly attaches to, the cylindrical wall.

While the depicted embodiment shows the housing being formed of two separate housing sections 30, 32 connected to the flow body 12, it is also possible that the housing be formed by a single casing or container with openings to accommodate the inlet port 14 and outlet port 16 of the flow body 12. With such a configuration, the fluid flow would still be able to pass through the flow path 20 and the aperture 26 between the viewing members 22.

The two viewing members 22 are held within the flow body 12 in receptacles 72 that position the windows 24 on opposing sides of the aperture 26. As illustrated in the schematic depiction of FIGS. 5 and 6, each of the viewing members 22 may include a spray element 34 around the respective windows 24. The spray elements 34 are preferably utilized to clean the windows by discharging a pressurized cleaning fluid onto the windows in order to remove any residue or particles that are limiting the observation of the fluid within aperture 26. In this regard, the spray element includes a plurality of cleaning ports 36 disposed about the periphery of the windows 24. Preferably, the spray elements 34 form an integral part of the respective annular metal frame 28 of the corresponding viewing member 22. Alternatively, however, the spray element 34 could be a distinct component surrounding the viewing member. In a preferred embodiment, the spray elements are configured as rings that have cleaning ports 36 completely surrounding the windows. However it should be understood that it is not necessary for the spray element 34 to be formed as an annular ring. Instead, the cleaning ports 36 could be provided in select strategic positions around the windows. Advantageously, the spray elements 34 are provided on each side of the aperture 26 within the flow body 10. This allows each spray element 34 to efficiently clean the window 24 of the opposing viewing member 22 by directly spraying the cleaning fluid across the aperture and onto the opposing window. This cross-spraying configuration also eliminates the need for any components of the spray element 34 from extending into the aperture 26 between the viewing members. Since the aperture 26 in some applications may be extremely narrow, for example, on the order of 500 microns, it can be important to keep components clear. Although a configuration with spray elements 34 on both sides of the flow body has proven advantageous, and several of the following embodiments of the invention are directed to configurations using opposing spray elements, other aspects of the invention are unrelated to the use of dual spray elements 34, and could be used with only one or without any spray elements.

In embodiments where spray elements 34 are employed, the cleaning fluid for the spray ports 36 can be provided to the spray elements 34 through a conduit 66 extending through the flow body 12. Advantageously, by using a conduit 66 that extends through the flow body 12, the cleaning fluid can be delivered to the spray elements 34 without having to pass through the internal areas of the flow analyzer housing that may contain sensitive electronic equipment. Specifically, the conduit 66 can extend from the flow body 12 directly into the corresponding viewing member 22 that houses the respective spray element 34. This configuration limits the need for using expensive connectors between both the surrounding environment into the flow analyzer housing and additional connectors from the interior of the housing into the viewing members 22. Instead, the cleaning fluid can enter the flow body through one connector disposed on an outer surface of the flow body, and then be passed to the respective viewing member through a simple passage at the interface between the flow body 12 and corresponding viewing member 22. As an additional advantage, the cleaning fluid conduit 66 can enter the flow body 12 through a single opening on the outer surface thereof using a single subsea connector, and be divided into branched constructions that deliver cleaning fluid to both viewing members 22. Alternatively, separate conduits can be associated with the spray element 34 of each viewing member 22. Preferably, at least a portion of the cleaning fluid conduit 66 is an annularly enclosed passage extending through the flow body. Such a conduit can be created by machining the passage into the flow body 12, for example by drilling. Alternatively, embodiments of the invention may use a configuration where the cleaning fluid is delivered through one or more pipes or tubes that extend through the analyzer housing and directly into the viewing members.

The flow body 12 may also include a wiring conduit 68 extending therethrough. The wiring conduit 68 may be used in combination with a flow body including the cleaning fluid conduit 66, or can be used in a flow body 12 that does not include the cleaning fluid conduit. The wiring conduit 68 extends across the flow body 12 from the illumination housing section 30 to the observation housing section 32. As schematically depicted in FIG. 6, the wiring conduit 68 provides an avenue for communications and power lines to extend between the housing sections. Preferably, the wiring conduit 68 extends from a first side of the flow body 12 to an opposing side of the flow body 12 in a direction that is substantially transverse the direction of the flow path 20 through the flow body. However, the wiring conduit 68 should be isolated from the flow path so that the contents in the flow path 20 cannot leak into the housing sections 30, 32. Preferably, this isolation is provided by a material wall of the flow body 12 separating the flow path 20 and wiring conduit 68. By including the wiring conduit 68 in the flow body 12, both power and control signals can be relayed from one of the housing sections to the other, thereby avoiding the necessity for each housing section to include an external wiring connection 70. In the illustrated embodiment, both power and data transmission are carried out through the single wiring connection 70 in the observation housing section 32. Both power and any necessary control signals are routed to the control unit 46 located in the observation housing section 32. From the control unit 46, power and control signals are sent to the imaging device 44 and to the illumination controller 42 via the wiring conduit. In turn, the illumination controller 42 sends power and control signals to the illumination device 40. Moreover, the imaging device 44 returns imaging data to the control unit 46. Of course, it is also possible for the control unit 46 to incorporate an illumination control module and send control and power signals directly to the illumination device 40. Furthermore, the illumination housing section 30 could include the wiring connection 70, and power and data signals could be sent through the wiring conduit to the observation housing section 32. Similar to the cleaning fluid conduit, at least sections of the wiring conduit 68 are preferably annularly enclosed. In this regard, the flow body 12 may be formed as a single integral piece and the wiring conduit 68 machined therein. Alternatively, the flow body 12 could be formed from pieces that are welded together in a manner that encloses the wiring conduit 68 therein.

Another advantageous feature that may be included in the flow body 12 are unique receptacles 72 for receiving the viewing members 22. The receptacles 72 are disposed on opposing sides of the flow body 12 and both hold the viewing members 22 and provide access of the viewing members 22 to the flow path 20. In certain embodiments, the receptacles 72 may be as simple as apertures positioned and sized to hold the windows 24 of the viewing members 22 at an appropriate distance apart. The viewing members can be secured into place and sealed around their periphery. Advantageously, both the securing and sealing can be provided by a circumferential weld around the viewing member. Alternatively, the sealing can be provided by independently from the fixation, for example using a o-ring and bolts. In a particularly advantageous embodiment, the receptacles 72 in the flow body 12 may include an internal thread and the viewing members 22 can include a corresponding external thread. When the viewing members are inserted into the respective receptacles, the threading can be used to carefully control the depth of insertion of the viewing members 22 into the flow body 12. Accordingly, the distance between the viewing windows 24 can be controlled to a very accurate degree before the viewing members can be fixed in place, for example by welding. This is particularly advantageous in embodiments where the distance between the windows 24 of the viewing members 22 is controlled to a very small aperture of, for example, about 500 microns.

Figure 8:
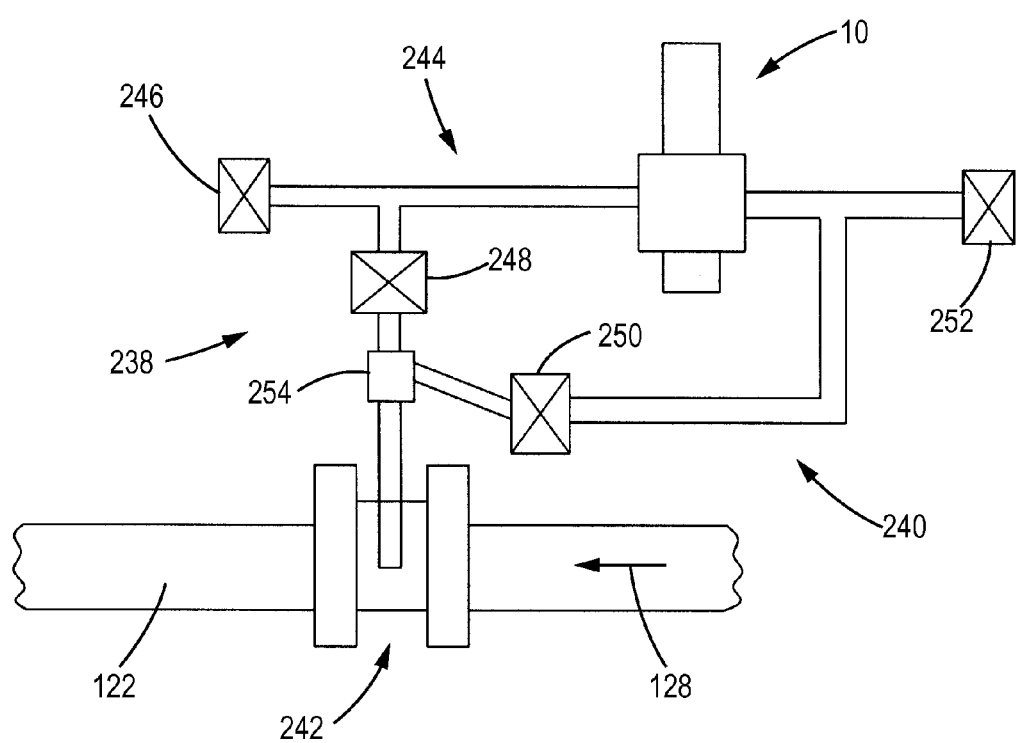
FIG. 8 shows a schematic view of a single entry point interface of a flow analyzer with a flow line in accordance with an embodiment of the invention.

FIG. 8 shows the flow analyzer 10 connected to a flow line 122 using a single-point entry sampler interface 242. In such embodiments, the flow line 122 need not be penetrated for both an intake line and a return line, such as shown in the embodiment of FIG. 2A. Instead, the flow line 122 is penetrated at only a single point, where sample fluid can be both extracted and returned to the flow line 122 using concentric lines, or another suitable extraction method known in the art. FIG. 8 also illustrates a dual-loop flow interface 238. Although the dual-loop flow interface 238 in FIG. 8 is shown with a single-point entry sampler interface 242, it is contemplated herein that the dual-loop flow interface can also be used in embodiments using a flow interface 138, such as shown in FIG. 2A.

Embodiments featuring a dual-loop interface 238, such as that illustrated in FIG. 8, can also be used to perform calibration or cleaning activities for the flow analyzer 10. The dual-loop interface 238 includes various valves for alternating flow between a primary loop 240 and a secondary loop 244. FIG. 8, for example, includes a first valve 246, a second valve 248, a third valve 250, and a fourth valve 252. The valves 246, 248, 250, 252 can be any suitable valve for selectively closing off or opening flow. In the illustrated embodiment, the primary loop 240 is active when the first valve 246 and the fourth valve 252 are in a closed position, and the second valve 248 and the third valve 250 are in open positions. In such a state, a sample fluid from the flow line 122 can be taken from the single-point entry sampler interface 242, drawn through the flow sampler 254, and into the primary loop 240 via the first and second valves 248, 250 to be introduced to the flow analyzer 10. In the primary loop, the flow analyzer 10 can be implemented to analyze the fluid flow 128 within the flow line 122. Alternatively, the secondary loop 244 is active when the first valve 246 and the fourth valve 252 are open, while the second valve 248 and the third valve 250 are closed. When the secondary loop 244 is active, the flow analyzer 10 is not in fluid communication with the fluid flow 128 in the flow line 122. This makes it possible to introduce cleaning solvents or calibration fluid into the flow analyzer 10 without introducing these fluids into the main flow line 122. Other system parameters, such as light intensity, can also be checked in this way. The systems desired for performing these cleaning and calibration activities can be connected to the first and fourth valves 244, 252, respectively, in a suitable manner. Additionally, it should be understood that, though the embodiment in FIG. 8 shows the dual-loop interface 238 using a single-point entry sampler interface 242, it is contemplated that another fluid interface, such as fluid interface 138 shown in FIG. 2A, could also be used.

While the various advantages described above of embodiments of the invention are set forth in the context of their benefits for use in harsh environments, many of these advantageous features would be beneficial in all environments. Accordingly, these embodiments are not limited to use in harsh environments and their advantages can be utilized for a wide variety of reasons.

While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above and below.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B," unless it is clear from the context or the foregoing description that only one of A and B is intended. Further, the recitation of "at least one of A, B and C" should be interpreted as one or more of a group of elements consisting of A, B and C, and should not be interpreted as requiring at least one of each of the listed elements A, B and C, regardless of whether A, B and C are related as categories or otherwise. Moreover, the recitation of "A, B and/or C" or "at least one of A, B or C" should be interpreted as including any singular entity from the listed elements, e.g., A, any subset from the listed elements, e.g., A and B, or the entire list of elements A, B and C.

What is claimed is:

1. A flow analyzer comprising:
   a flow body having a single-piece construction of material, the flow body including a flow path extending through the flow body along a flow direction between opposing inlet and outlet ports;
   first and second viewing members respectively disposed on the first and second sides of the flow path that extends through the flow body, each of the first and second viewing members including a window;
   a light source disposed on the first side of the flow body and configured to illuminate fluid within the flow path through the first viewing member;
   a camera disposed on a second side of the flow body and configured to visually observe the fluid within the flow path through the second viewing member; and
   first and second spray elements respectively associated with the first and second viewing members, each spray element being configured to spray a cleaning fluid on the window of the opposing viewing element;
   wherein the flow body includes a branched cleaning fluid conduit having a single inlet opening that is in fluid communication with each of the first and second spray elements so as to provide cleaning fluid to each of the first and second spray elements from the single inlet opening, and
   wherein the flow body includes a wiring conduit extending through the flow body substantially transverse to the flow direction from the first side of the flow body to the second side of the flow body for electrically connecting the camera with the light source, the wiring conduit being isolated from the flow path.

2. The flow analyzer of claim 1, wherein the flow body is a single monolithic structure.

3. The flow analyzer of claim 1, further comprising a housing formed by the flow body and first and second housing sections, the first housing section being attached to the first side of the flow body and enclosing the light source and the second housing section being attached to the second side of the flow body and enclosing the camera.

4. The flow analyzer of claim 3, wherein the housing includes a single external wiring connection.

5. The flow analyzer of claim 1, further comprising a computational unit configured to analyze image data from the camera.

6. The flow analyzer of claim 1, wherein the light source includes an illumination controller.

7. The flow analyzer of claim 6, wherein the illumination controller includes a strobe unit.

8. The flow analyzer of claim 6, wherein the light source includes at least one LED.

9. The flow analyzer of claim 1, wherein the flow body includes opposing first and second receptacles receiving the first and second viewing members, the first and second receptacles including inner threads and the first and second viewing members including corresponding outer threads, the inner and outer threads being adapted for accurately positioning the first and second viewing members at a preselected distance from one another.

* * * * *